United States Patent [19]

Wehner et al.

[11] Patent Number: 4,554,367

[45] Date of Patent: Nov. 19, 1985

[54] PHOSPHONIUM ORGANOHALOGENOSTANNATES-IV

[75] Inventors: Wolfgang Wehner, Zwingenberg; Reinhardt Grade, Bensheim, both of Fed. Rep. of Germany

[73] Assignee: Ciga-Geigy Corporation, Ardsley, N.Y.

[21] Appl. No.: 535,528

[22] Filed: Sep. 26, 1983

[30] Foreign Application Priority Data

Oct. 6, 1982 [CH] Switzerland .......................... 5875/82

[51] Int. Cl.⁴ ................................................. C07F 7/22
[52] U.S. Cl. ...................................... 556/20; 514/493; 71/86; 71/97; 252/8.6; 106/18.31; 106/287.19
[58] Field of Search ........................................ 260/429.7

[56] References Cited

U.S. PATENT DOCUMENTS

| 3,259,541 | 7/1966 | Schröder et al. | 260/429.7 X |
|---|---|---|---|
| 3,355,439 | 11/1967 | Welch et al. | 260/429.7 X |
| 3,448,127 | 6/1969 | Dötzer | 260/429.7 X |
| 3,502,690 | 3/1970 | Schröder et al. | 260/429.7 X |
| 4,052,426 | 10/1977 | Wehner et al. | 260/429.7 |
| 4,462,935 | 7/1984 | Onopchenko et al. | 260/429.7 |

FOREIGN PATENT DOCUMENTS 1802375 11/1970 Fed. Rep. of Germany .

OTHER PUBLICATIONS

J. W. Nicholson, Coord. Chem. Rev. 47, 263, (1982).
S. N. Bhattacharya et al., Indian J. Chem., 19A, 592, (1980).
B. A. Richardson, Stone Industries 8, 22, (1973).

*Primary Examiner*—Helen M. S. Sneed
*Attorney, Agent, or Firm*—Luther A. R. Hall

[57] ABSTRACT

Phosphonium stannates of the formula I $$[(R^1)_a(R^2)_bP]_n^{\oplus}[R_q^3SnX_rY_t]_w^{n\ominus} \qquad (I),$$

in which the symbols $R^1$, $R^2$, $R^3$, X, Y, a, b, n, q, r, t and w are as defined in the description, are active biocides. They can be used both in the preservation of materials and for protecting crop plants. Their water-solubility and their low volatility are particularly valuable properties.

5 Claims, No Drawings

PHOSPHONIUM ORGANOHALOGENOSTANNATES-IV

The present invention relates to novel phosphonium stannate complexes which are distinguished by a very good biocidal activity.

It is known that phosphonium salts, organo-tin salts and certain phosphonium stannates can be used as biocides.

A general survey of the chemistry of organostannate-IV complexes is given by J. W. Nicholson in Coord. Chem. Rev. 47, 263 (1982).

U.S. Pat. No. 3,448,127 describes a general method for the preparation of onium salt complexes. However, phosphonium stannates and their activity as biocides are not described.

S. N. Bhattacharya et al, Indian J. Chem., 19A, 592 (1980) discloses compounds similar to the phosphonium stannate described here.

It is known from U.S. Pat. No. 3,259,541 that phosphonium stannate of the formula $[R^1R^2R^3R^4P]$ [Phenyl$_3$SnXY], in which $R^1$–$R^4$ are, inter alia, $C_1$–$C_{12}$-alkyl and X and Y, inter alia, halogen, have biocidal properties.

German Offenlegungsschrift No. 1,802,375 also describes fungicidally active systems consisting of a phosphonium stannate and a metal salt of an alkylene-bis(dithiocarbamate).

The present invention relates to phosphonium stannates of the general formula I

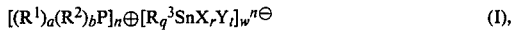

$$[(R^1)_a(R^2)_bP]_n^\oplus [R_q^3SnX_rY_t]_w^{n\ominus} \quad (I),$$

in which $R^1$ is $C_1$–$C_6$-alkyl, or $C_1$–$C_6$-alkyl which is substituted by one hydroxyl or cyano group, one or two $C_2$–$C_{22}$-alkoxy carbonyl or $C_2$–$C_{22}$-alkylcarbonyloxy groups or one halogen atom, or is $C_3$–$C_7$-cycloalkyl or phenyl, and $R^2$ is hydrogen, $C_8$–$C_{22}$-alkyl, methylol, or benzyl which is substituted by one or two $C_1$–$C_{14}$-alkyl groups, one or two chlorine atoms or one or two nitro groups, or is benzyl, with the proviso that $R^1$ is not phenyl and $R_3^3$ is not methyl, ethyl, n-propyl, n-butyl or phenyl, or in which $R^2$ is a group of the formula II

$$-ZPR_3^1 \quad (II)$$

in which $R^1$ is as defined above and Z is a straight-chain or branched ($C_{22-22}$—$H_{4-44}$) group, which can be interrupted by one or more —O—, —S—, —O—C(O)—, —C(O)—O— or —N(R⁴)—groups, in which R⁴ is hydrogen or $C_1$–$C_4$-alkyl, and $R^3$ has the same meaning as $R^1$, or is benzyl, benzyl which is substituted by one or two $C_1$–$C_{14}$-alkyl groups, one or two chlorine atoms or one or two nitro groups, or is 2-methyl-2-phenylpropyl, with the proviso that the radicals $R^1$ and/or $R^3$ are other than phenyl if X and/or Y are not fluorine, and X and Y independently of one another are fluorine, chlorine, bromine, iodine. cyanate, thiocyanate or carboxylate of the formula $R^5$—COO—, in which $R^5$ is hydrogen, or is straight-chain or branched $C_1$–$C_{18}$-alkyl, which can be unsubstituted or substituted by one to three halogen atoms or one to three hydroxyl or amino groups, or is phenyl, which is unsubtituted or substituted by one to three halogen atoms or one to three amino, nitro, hydroxyl or $C_1$–$C_4$-alkoxy groups, or is $C_5$–$C_8$-cycloalkyl or a substituted or unsubstituted pyridine radical, and in which n is 1 or 2, q is 1, 2, or 3, a can assume the value 3 or 4, the value 4 only being permitted if X and/or Y are fluorine, b can assume the value 1 or 4, the value 4 only appearing if X and/or Y are fluorine, the sume (a+b) must always be 4, r and t are integers from 0 to 5, the sum (r+t) being 2 to 5 and the sum (q+r+t) corresponding to the value (n+4), and w is 2, if $R^2$ is a group of the formula II, or is otherwise 1.

Examples of $C_1$–$C_6$-alkyl $R^1$ and $R^3$, $C_8$–$C_{22}$-alkyl $R^2$ and $C_1$–$C_{18}$-alkyl $R^5$ are straight-chain or branched alkyl radicals such as methyl, ethyl, n-propyl, isopropyl, n-butyl, sek.butyl, n-amyl, isoamyl, n-hexyl, n-octyl, 2-ethylhexyl, decyl, undecyl, dodecyl, tridecyl, tetradecyl, hexadecyl, octadecyl, eicosyl or docosyl. The present invention also relates to mixtures of alkyl groups such as tetradecyl and hexadecyl.

Examples of substituted $C_1$–$C_6$-alkyl $R^1$ and $R^3$ are methylol, 2-hydroxyethyl, 4-hydroxybutyl, 6-hydroxyhexyl, Cyanomethyl, 2-cyanoethyl, 4-chlorobutyl, butoxycarbonylethyl, di-(octyloxycarbonyl)-methyl, methoxycarbonylhexyl, di(butoxycarbonyl)-methyl, undecylcarbonyloxyethyl, 3-chloro-2-undecylcarbonyloxy-propyl and 2-hydroxy-2-undecylcarboyloxyethyl.

$C_3$–$C_7$-cycloalkyl $R^1$ and $R^3$ and $C_5$–$C_8$-cycloalkyl $R^5$ are, in particular, cyclopropyl, cyclobutyl, cyclopentyl, cyclohexyl, cycloheptyl and cyclooctyl. Cyclopentyl and cyclohexyl are preferred, and cyclopentyl is particularly preferred.

$R^2$ and $R^3$ can be substituted or unsubstituted benzyl, such as o-, m- or p-methylbenzyl, 2,3-, 3,4-, 3,5- or 2,5-dimethylbenzyl, nonylbenzyl, laurylbenzyl, tetradecylbenzyl, o-, m- or p-chlorobenzyl, 2,3-, 3,4-, 3,5- or 2,5-dichlorobenzyl, o-, m- or p-nitrobenzyl or 2,3-, 3,4-, 3,5- or 2,5-dinitrobenzyl.

In a —$ZPR_3^1$ group $R^2$, Z is, for example, ethylene, 1,3-trimethylene, 1,4-tetramethylene, propylidene, —$CH_2CH_2$—O—$CH_2CH_2$—, —($CH_2CH_2O)_4CH_2CH_2$—, —$CH_2CH_2$—NH—$CH_2CH_2$—, —$CH_2CH_2$—N($CH_3$)—$CH_2CH_2$— or —$CH_2COOCH_2CH_2$.

Compounds in which $R^2$ is —$ZPR_3^1$ are preferred.

Examples of $C_{1/-C_4}$-alkyl $R^4$ are methyl, ethyl, n-propyl, isopropyl, n-butyl-sec.-butyl and tert.-butyl.

Examples of substituted $C_1$–$C_{18}$-alkyl $R^5$ are methylol, 2-hydroxyethyl, 4-hydroxybutyl, 6-hydroxyhexyl, 2-hydroxyoctadecyl, chloromethyl, 2-chloroethyl, 1,2-dichloroethyl, 4-chlorobutyl, 6-chlorohexyl, 2-chlorooctadecyl, aminomethyl, 2-aminoethyl, 4-aminobutyl, 6-aminohexyl and 2-aminooctadecyl. Examples of substituted phenyl $R^5$ are o-, m- or p-substituted chloro-, amino-, nitro-, methoxy-, ethoxy,- n-propoxy- or n-butoxy-phenyl, 2,3-, 3,4-, 3,5- or 2,5-dichloro, -dinitro-, -diamino-, -dimethoxy-, diethoxy-, di-n-propoxy-, -di-n-butoxy-phenyl, 2-chloro-3-nitrophenyl, 3-amino-4-ethoxyphenyl, 3-amino-5-ethoxyphenyl, 2,4,6-triaminophenyl and 2,4,6-trichlorophenyl. Examples of substituted or unsubstituted pyridine radicals $R^5$ are pyridine-2-, -3-, or -4-carboxylic acid and 2-, 3- or 4-methylpyridine.

Preferred compounds are those of the formula I in which $R^3$ is $C_1$–$C_6$-alkyl, $C_1$–$C_6$-mono- or -dihydroxyalky, $C_3$–$C_7$-cycloalkyl or 2-methyl-2-phenylpropyl and the other symbols are as defined above.

Particularly preferred compounds of the formula I are those in which $R^1$ is n-butyl, methylol or phenyl, $R^2$ is $C_8$–$C_{16}$-alkyl, 3,4-dichlorobenzyl or p-nitrobenzyl and $R^3$ is $C_1$–$C_4$-alkyl, cyclohexyl or phenyl, with the proviso that the radicals $R^1$ and/or the radicals $R^3$ are other than phenyl if X and/or Y are not fluorine, and the other symbols are as defined above.

Compounds of the formula I which are of particular interest are those in which $R^1$ and $R^3$ are n-butyl, $R^2$ is $C_{12}$–$C_{16}$-alkyl and X and Y independently of one another are fluorine or chlorine, and also those in which $R^1$ and $R^3$ are n-butyl, $R^2$ is tetradecyl, X and Y independently of one another are fluorine or chlorine, q is 3 and n, r and t are 1, and those in which q is 3, n and r are 2 and t is 1.

Compounds of the formula I which are also of interest are those in which X and/or Y are fluorine. In addition, compounds of the formula I in which X and/or Y are chlorine are of interest. Other preferred compounds of the formula I are those in which X and/or Y are bromine. Compounds of the formula I in which the radicals X and/or Y are carboxylates of the formula $R^5$—COO—, but especially benzoate, propionate or naphthenate. Compounds of the formula I in which $R^1$ and $R^3$ are n-butyl, $R^2$ is tetradecyl, X and Y are fluorine or chlorine and n, q, r and t are 2 are also of interest.

Compounds of the formula I in which $R^1$ and $R^3$ are n-butyl, $R^2$ is tetradecyl, X and Y are fluorine or chlorine, n, q and t are 1 and r assumes the value 3 are also of importance.

Compounds of the formula I in which $R^1$ and $R^3$ are n-butyl, $R^2$ is $C_{12}$–$C_{16}$-alkyl, X is fluorine or chlorine, q is 3, r is 2, n is 1 and t assumes the value 0 receive further attention.

Compounds in which q is 3 are preferred.
Compounds of the formula V

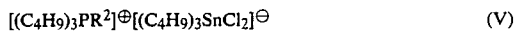

$$[(C_4H_9)_3PR^2]^{\oplus}[(C_4H_9)_3SnCl_2]^{\ominus} \quad (V)$$

in which the radical $R^2$ is $C_{12}$–$C_{14}$-alkyl, are also of interest.

Compounds of the formula VI

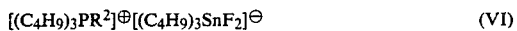

$$[(C_4H_9)_3PR^2]^{\oplus}[(C_4H_9)_3SnF_2]^{\ominus} \quad (VI)$$

in which the radical $R^2$ is $C_{12}$–$C_{14}$-alkyl, are likewise preferred.

Compounds of the formula VII

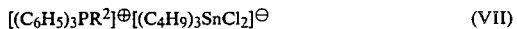

$$[(C_6H_5)_3PR^2]^{\oplus}[(C_4H_9)_3SnCl_2]^{\ominus} \quad (VII)$$

in which the radical $R^2$ is $C_{12}$–$C_{14}$-alkyl, are moreover of interest.

Compounds of the formula VIII

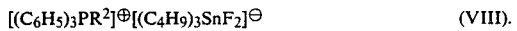

$$[(C_6H_5)_3PR^2]^{\oplus}[(C_4H_9)_3SnF_2]^{\ominus} \quad (VIII).$$

in which the radical $R^2$ is $C_{12}$–$C_{14}$-alkyl, are additionally preferred.

The phosphonium stannates of the present invention can be prepared, for example, by reacting approximately n/w mole of a phosphonium salt of the formula III

$$[R_3^1 R^2 P]^{\oplus} X^{\ominus} \quad (III)$$

in which $R^1$, $R^2$ and X are defined above, with approximately 1 mole of a tin salt of the formula IV

$$R_q^3 SnY_t \quad (IV),$$

in which $R^3$, Y, q and t are as defined above.

The phosphonium halides of the formula III are commercial products, or they can be prepared by known methods from the corresponding phosphines and an organic halide. The tin salts of the formula IV are likewise commercially available products.

The reaction of the phosphonium halide of the formula III with the organo-tin halide is advantageously carried out at room temperature, with or without a solvent, for example methanol, ethanol, chloroform, acetone, methylene chloride, toluene, xylene, water and the like (homogeneous or 2-phase system). If a solvent is used, this can be evaporated off after the reaction, or the reaction product is precipitated, for example by addition of an ether, and the resulting product can be purified by recrystallization.

The compounds of the formula I are distinguished by their low volatility and good water-solubility.

The compounds according to the invention provide a broad action spectrum in the control of animal and plant pests, which results in various possible uses, for example as bactericides or disinfectants, against the formation of slime in paper production and as fungicides, insecticides, acaricides, herbicides or algicides. They are ideal products for water treatment, for controlling microorganisms, or cleaning cooling water systems and/or for preventing the formation of slime by bacteria. The novel substances are also outstandingly suitable as industrial antimicrobial agents for preservation of materials, for example for the preservation of wood, pulp and paper, textiles and leder, paints, varnishes, antifouling paints and similar coating materials, optical glasses and other types of glasses, plastics, rubber and adhesives, boring and cutting oils, mineral oil, lubricants, waxes, fuels and other materials.

The compounds are employed in the concentration ranges known to the expert, depending on the intended use. The limits of the concentrations used are given by the following values: whilst concentrations in only the ppm range are sufficient in cooling water, concentrations of up to 40% by weight are usual in antifouling recipes.

The compounds can be applied as dusts, sprinkling powders or mists, in the pure form or together with carriers. They can also be suspended in liquid coating agents and the like, and. if necessary for the formation of uniform dispersions, wetting agents or emulsifiers can promote the uniform distribution of the active substance. Other biocides, such as insecticides, may also be added.

A preferred field of application is protective paints, especially antifouling paints, or an organic basis which contain, in addition to the conventional base substances and additives, 0.5–60% by weight, preferably 3–25% by weight, based on the total mixture, of a compound of the formula I or of mixtures thereof.

Conventional base substances for antifouling paints are the coating raw materials called binders and known to the expert, such as natural and synthetic resins, homopolymeric and copolymeric products obtained from the monomers vinyl chloride, vinylidene chloride, styrene, vinyl toluene, vinyl esters and acrylic acids and methacrylic acids and esters thereof, and furthermore chlorinated rubber, natural or synthetic rubber, which may be chlorinated or cyclised, and also reactive resins, such as epoxide resins, polyurethane resins and unsaturated polyesters, which may, if appropriate, be converted into film-forming products of higher molecular weight by addition of hardeners.

The binders can be in liquid or dissolved form. In the case of dissolved binders, including thermoplastics, a protective film may also be formed by evaporation of the solvent. Solid coating agents can be applied to objects by, for example, the powder coating method. Examples of other conventional base substances are tar, modifiers, dyes, inorganic or organic pigments, fillers and hardeners.

It has also been found that compounds having the structure of the formula I have a microbicidal spectrum for protecting crop plants which is very favourable for practical requirements. In the context of the present invention, examples of crop plants are cereals, maize, rice, vegetables, sugarbeet, soybean, groundnut, fruit trees, ornamental plants, vines, hops, cucumber-type plants (cucumbers, pumpkins and melons), solanaceae, such as potatoes, tobacco and tomatoes, and also banana, cocoa and natural rubber plants.

The fungi or bacteria which occur on plants or parts of plants (fruit, blossom, foliage, stem, tubors and roots) of these and related useful crops can be checked or destroyed using the active substances of the formula I, parts of the plants which additionally grow later also remaining protected from such microorganisms. The active substances are effective against the phytopathogenic fungi belonging to the following classes: Ascomycetes (for example Erysiphaceae, Fusarium); Basidiomycetes, such as Puccinia and *Fungi imperfecti* (for example Cercospora and Septoria); and Phycomycetes, such as Phytophtora. The compounds of the formula I moreover have a systemic action. They are advantageously used as dressing agents for treatment of seed and stored products (fruits, tubors and grain) and plant cuttings, for protection from fungal infections, and against phytopathogenic fungi occurring in the soil.

They are also effective against phytopathogenic bacteria, for example Pseudomonas sp. and Xanthomonas sp.

The compounds of the formula I are used in plant protection by themselves or together with suitable carriers and/or other adjuvants. Suitable carriers and adjuvants can be solid or liquid and are the substances conventionally employed in the art of formulation, for example natural or regenerated mineral substances, solvents, dispersants, wetting agents, tackifiers, thickeners, binders or fertilizers.

The content of active substance in marketable compositions is between 0.1 and 90%.

For application, the compounds of the formula I can be in the following formulations (the percentage by weight data in brackets being advantageous amounts of active substance):
solid formulations: dusts and sprinkling powders (up to 10%), granules, coated granules, impregnated granules and homogeneous granules, pellets (grains) (1 to 80%). Liquid formulations:
(a) active substance concentrates which are dispersible in water: wettable powders and pastes (25–90% in the commercial pack, 0.01 to 15% in the ready-to-use solution), emulsion and solution concentrates (10 to 50%; 0.01 to 15% in the ready-to-use solution); and
(b) solutions (0.1 to 20%); aerosols.

The invention thus furthermore relates to compositions containing the compounds according to the invention, the use of the compounds according to the invention and compositions for controlling microorganisms, insects, molluscs and algae in the preservation of materials.

The biocidal mixtures which can be used according to the invention can also contain other active substances.

Examples of these are:
(a) Organo-sulfur compounds, for example methylene dithiocyanate (MBT), isothiazolones or 3,5-dimethyltetrahydro1,3,5-2H-thiadiazone-2-thione (DMTT). Such substances are used, in particular, against the formation of slime in paper production.
(b) Chlorinated phenols, such as sodium pentachlorophenolate. Such compounds are distinguished by a broad action spectrum.
(c) Copper salts, such as copper sulfate, are algicides which are effective in small amounts.
(d) 2,2-Dibromo-3-nitrilopropionamide (DBNPA) as an algicide, fungicide and bactericide.
(e) Chlorine and bromine are known effective algicides and bactericides which are used, in particular, for water treatment.
(f) Chlorine dioxide, chlorine isocyanurate and hypochlorites are also current biocides for water treatment.
(g) Wood biocides
   a. Salt mixtures based on silicofluorides, hydrogenfluorides, inorganic boron compounds, chromates, fluorides, arsenic (oxide and arsenates), copper salts (sulfate and naphtheante), tin salts and zinc salts and mercury compounds.
   b. Tar oil products
   c. Organic active substances, such as pentachlorophenol, phenol, DDT, dieldrine, lindane or Gammexane and chlorinated naphthalene.
(h) Disinfectants
   a. Phenol or phenol derivatives
   b. Formaldehyde and/or other aldehydes and derivatives
   c. Chlorine and organic or inorganic substances with active chlorine
(d). Amphoteric surfactants.

Such formulations can, of course, also contain other substances and assistants, such as are conventionally also used in such formulations. These include, for example, cationic or non-ionic surface-active substances, electrolytes, complexing agents, solubilizing agents, dyes and fragrances. These additives serve, for example, to improve the wetting power and stability to hardening, to adjust the viscosity and to increase the stability of the solutions to low temperatures.

The following examples illustrate the invention in more detail, without restricting its scope. Percentages (%) and parts given in these examples are by weight.

Examples of compounds of the formula I are:

| Example | $R_a{}^1$ | $R_b{}^2$ | $R_q{}^3$ | $X_r$ | $Y_t$ | melting point (°C.) |
|---|---|---|---|---|---|---|
| 1 | Butyl$_3$ | Benzyl$_1$ | Butyl$_3$ | Cl$_2$ | — | 86–88 |
| 2 | Butyl$_3$ | Benzyl$_1$ | Cyclohexyl$_3$ | Cl$_2$ | — | 109–111 |
| 3 | Butyl$_3$ | Tetradecyl$_1$ | Butyl$_3$ | Cl$_2$ | | |
| 4 | Butyl$_3$ | Tetradecyl$_1$ | Cyclohexyl$_3$ | Cl$_2$ | — | Oil |
| 5 | Butyl$_3$ | Tetradecyl$_1$ | Phenyl$_3$ | Cl$_2$ | — | Oil |
| 6 | Butyl$_3$ | p-Nitrobenzyl$_1$ | Cyclohexyl$_3$ | Cl$_1$ | BR$_1$ | 116–118 |
| 7 | Butyl$_3$ | 3,4-Dichlorbenzyl$_1$ | Cyclohexyl$_3$ | Cl$_2$ | — | 120–122 |
| 8 | Meth- | Lauryl- | Butyl$_3$ | Cl$_2$ | — | Oil |

-continued

| Example | $R_a^1$ | $R_b^2$ | $R_q^3$ | $X_r$ | $Y_t$ | melting point (°C.) |
|---|---|---|---|---|---|---|
| 9 | Methylol$_3$ | Laurylbenzyl$_1$ | Cyclohexyl$_3$ | Cl$_2$ | — | Wax |
| 10 | Methylol$_3$ | Laurylbenzyl$_1$ | Phenyl$_3$ | Cl$_2$ | — | Wax |
| 11 | Butyl$_3$ | Tetradecyl$_1$ | Methyl$_2$ | Cl$_3$ | — | Oil |
| 12* | Butyl$_3$ | Tetradecyl$_1$ | Methyl$_2$ | Cl$_4$ | — | Oil |
| 13 | Butyl$_3$ | Tetradecyl$_1$ | Methyl$_1$ | Cl$_4$ | — | Oil |
| 14* | Butyl$_3$ | Tetradecyl$_1$ | Methyl$_1$ | Cl$_5$ | — | Oil |
| 15 | Butyl$_3$ | Tetradecyl$_1$ | Butyl$_1$ | Cl$_4$ | — | Wax |
| 16* | Butyl$_3$ | Tetradecyl$_1$ | Butyl$_1$ | Cl$_5$ | — | Oil |

*: n = 2

In the above Table, butyl is n-butyl, tetradecyl is n-tetradecyl and laurylbenzyl is a mixture of the o-, m- and p-isomers.

EXAMPLE 17

9.7 parts of triphenylbenzylphosphonium chloride are dissolved in 80 parts of methanol, and a solution of 10.1 parts of tricyclohexyl-tin chloride in 100 parts of acetone is added. After the volatile constituents have been stripped off, 19.8 parts of a colourless crystalline substance of melting point 193°–195° C. remain. In the $^{119}$SnNMR spectrum, a CDCl$_3$ solution of the substance obtained, i.e. triphenylbenzylphosphonium tricyclohexyldichlorostannate, shows a shift of 48.9 ppm towards the higher field compared with tricyclohexyl-tin chloride.

EXAMPLE 18

Tri-n-butyl-n-tetradecyl-phosphonium chloride and tricyclohexyl-tin chloride are reacted in a similar manner. In the $_{119}$SnNMR spectrum, the tri-n-bytyl-n-tetradecyl-phosphonium tricyclohexyldichlorostannate thereby formed shows a shift of 52.7 ppm towards the higher field (CDCl$_3$) solution) compared with tricyclohexyl-tin chloride.

EXAMPLE 19

Tri-n-butyl-n-hexadecylphosphonium tricyclohexylbromochlorostannate is obtained in a similar manner. The shift for this substance is 36.1 ppm towards the higher field compared with tricyclohexyl-tin chloride.

EXAMPLES 20–51

The following complexes are obtained in a similar manner, with appropriate choice of the phosphonium and tin components:

TABLE A

| Example | Phosphonium cation(*1) | Stannate anion(*1) | Sn—NMR shift in CDCl$_3$ [ppm] | NMR standard(*2) | Properties or melting point (°C.) |
|---|---|---|---|---|---|
| 20 | Tributyltetradecyl | Dimethyltrichloro | | | highly viscous oil |
| 21 | Di-(tributyltetradecyl) | Dimethyltetrachloro | | | highly viscous oil |
| 22 | Tributyltetradecyl | Methyltetrachloro | | | highly viscous oil |
| 23 | Di-(tributyltetradecyl) | Methylpentachloro | | | highly viscous oil |
| 24 | Tributyltetradecyl | Butyltetrachloro | −262.4 | d | Wax |
| 25 | Di-(tributyltetradecyl) | Butylpentachloro | −282.6 | | viscous oil |
| 26 | Tetrakis-hydroxymethyl | Tricyclohexyldichloro | | | 122–124 |
| 27 | Tributyltetradecyl | Tributylchlorofluoro | −67.4 | g | highly viscous oil |
| 28 | Tributyltetradecyl | Tributyldifluoro | −22.7 | g | highly viscous oil |
| 29 | Bis-(tributyl)-decamethylene | Bis-(tributylbromochloro) | | | viscous oil |
| 30 | Tributylhexadecyl | Tricyclohexylbromochloro | −36.1 | b | highly viscous |
| 31 | Tributylmethyl | Tricyclohexyldichloro | −157.4 | b | 78–80 |
| 32 | Tributylmethyl | Tricyclohexyliodochloro | | | 105–106 |
| 33 | Triphenylmethyl | Tricyclohexyliodochloro | −11.7 | b | 175–176 |
| 34 | Diphenylformylmethyl | Tricyclohexyldichloro | −19.4 | b | 195–196 |
| 35 | Tetrabutyl | Tricyclohexyldichloro | −42.7 | b | 136–137 |
| 36 | Tetraphenyl | Tricyclohexylbromochloro | −25.5 | b | 198–200 |
| 37 | Tributyltetradecyl | Triphenylchlorofluoro | | | 171–173 |
| 38 | Triphenylcyclopropyl | Tricyclohexylbromochloro | −20.1 | b | 98–100 |
| 39 | Triethylhydrido | Tricyclohexyldichloro- | −24.3 | b | 140–142 |
| 40 | Triethyllauryl | Tricyclohexylbromochloro | −47.7 | b | highly viscous |
| 41 | Tributylmethyl | Tributyldichloro | −200.2 | a | Wax |
| 42 | Tributylmethyl | Tributyliodochloro | −53.0 | a | highly viscous |
| 43 | Triphenylmethyl | Tributyliodochloro | −77.1 | a | highly viscous |
| 44 | Tetraphenyl | Tributylbromochloro | −123.9 | a | 121–123 |
| 45 | Tetrabutyl | Tributyldichloro | −153.8 | a | 70–72 |
| 46 | Tributylmethyl | Trimethyldichloro | −223.7 | e | 75–76 |
| 47 | Tributyltetradecyl | Dibutyltrichloro | −242.0 | f | highly viscous |
| 48 | Tetrabutyl | Tributyldifluoro | −62.6 | g | 153–156 |
| 49 | Tetrabutyl | Tributylchlorofluoro | −78.9 | g | 128–129 |
| 50 | Triphenylchloromethyl | Tricyclohexyldichloro | | | 162–164 |

TABLE A-continued

| Example | Phosphonium cation[*1] | Stannate anion[*1] | Sn—NMR shift in CDCl$_3$ [ppm] | NMR standard[*2] | Properties or melting point (°C.) |
|---|---|---|---|---|---|
| 51 | Triphenyllauryl | Triphenylbromofluoro | | | 177–178 |

[*1]Butyl is n-butyl, Lauryl is n-lauryl and Tetradecyl is n-tetradecyl

[*2]NMR Standards: a is tributyl-tin chloride, b is tricyclohexyl-tin chloride, c is triphenyl-tin chloride, d is butyl-tin trichloride, e is trimethyl-tin chloride, f is dibutyl-tin dichloride and g is tributyl-tin fluoride

EXAMPLE 52

Determination of the minimum inhibitory concentration (MIC) against bacteria

ONCs (cultures incubated overnight) of the bacteria strains A–F grown in Caso-Peptone broth (Merck) are each diluted 1:1,100 in saline. An amount of the suspension is introduced into Caso-Peptone broth such that the bacteria are again diluted 1:1,000. The cultures are treated with 100 or 300 mg/liter of the phosphonium stannates shown in Table B. After incubation at 30° C. in a shaking water bath for 24 hours, the cultures are evaluated on the basis of cloudiness. The MIC is the concentration at which the broth is not clouded by bacterial growth.

TABLE B

| MIC (mg/liter) Stannate Example No. | Bacteria strain* | | | | | |
|---|---|---|---|---|---|---|
| | A | B | C | D | E | F |
| 3 | 100 | 100 | 100 | 100 | 100 | 100 |
| 5 | 100 | 100 | 100 | 100 | 100 | 100 |
| 20 | 100 | 100 | 100 | 100 | 100 | 100 |
| 21 | 100 | 100 | 100 | 100 | 100 | 100 |
| 22 | 100 | 100 | 100 | 100 | 100 | 100 |
| 23 | 100 | 100 | 100 | 100 | 100 | 100 |
| 24 | 100 | 100 | 100 | 100 | 100 | 100 |
| 25 | 100 | 100 | 100 | 100 | 100 | 100 |
| 8 | 100 | 100 | >300 | >300 | >300 | 100 |
| 37 | 100 | 100 | 100 | 100 | 100 | 100 |
| 27 | 100 | 100 | 100 | 100 | 100 | 100 |

*A: Proteus vulgaris
B: Pseudomonas aeruginosa
C: Enterobacter aerogenes
D: Serratia marcenscens
E: Alkaligenes denitrificans
F: Bacillus subtilis The good growth-inhibiting action of the compounds, in particular even against the Gram-negative bacteria, which are difficult to control, can be seen from Table B.

EXAMPLE 53

Determination of the minimum destruction concentration against a mixed bacteria culture To prepare the mixed culture, amounts of the ONCs, grown in Case-Peptone broth, of the various bacteria strains: *Escherichia coli*, *Bacillus cereus* var. mycoides, *Staphylococcus aureus*, *Pseudomonas aeruginosa*, *Enterobacter aerogenes* and *Proteus vulgaris*, are each introduced into Tyrode's solution such that a final dilution of 1/1,000 is achieved, and the mixed culture is incubated at 30° C. in a shaking water bath for 5 hours.

5 µl are then withdrawn from the samples and dripped onto Caso-Peptone agar. After renewed incubation at 30° C. for 24 hours, the growth is evaluated visually.

As can be seen from the following Table, the phosphonium stannates also have a powerful bactericidal action against these slime-forming bacteria.

TABLE C

| | Destruction of a mixed bacteria culture in Tyrode's solution | | | |
|---|---|---|---|---|
| | Growth | | | |
| No. | 10 | 30 | 60 | 100 mg/liter |
| 5 | + | (−) | − | − |
| 8 | + | + | + | (+) |
| 24 | + | (+) | − | − |
| 25 | + | − | − | − |
| 3 | + | − | − | − |

+ = growth, no destruction
(+) = growth, little control (greater than 10 colonies), slight destruction
(−) = slight growth (1–10 colonies)
− = no growth, destruction

EXAMPLE 54

Determination of the minimum inhibitory concentration (MIC) against fungi

The investigation is carried out in malt extract agar (Merck) by the known agar incorporation test using the fungi
G *Aspergillus niger*
H *Aspergillus phoenicia*
I *Penicillium funiculosum*
J *Alternaria alternata*
K *Cladosporium cladosporioides*
J *Candida albicans*
M *Endomyces geotrichum*
N *Aureobasidium pullulans*
O *Chaetomium globosum*.

For inhibition, the various compounds are in each case added in amounts such that concentrations of 10, 50 and 100 ml/liter results in the agar. The concentrations (mg/liter) required for inhibition of the growth of the fungi (starting from traces of fungi dripped on) are illustrated in Table D.

TABLE D

| | Determination of the MIC against fungi | | | | | | | | |
|---|---|---|---|---|---|---|---|---|---|
| | Strain | | | | | | | | |
| No. | G | H | I | J | K | L | M | N | O |
| 5 | 10 | 10 | 50 | 10 | 10 | 10 | 10 | 10 | 50 |
| 20 | 50 | 50 | 10 | 50 | 10 | 10 | 10 | 10 | 10 |
| 21 | 50 | 50 | 10 | 50 | 10 | 10 | 10 | 10 | 10 |
| 22 | 50 | 50 | 10 | 50 | 10 | 10 | 10 | 10 | 10 |
| 23 | 50 | 50 | 10 | 50 | 10 | 10 | 10 | 10 | 10 |
| 8 | 10 | 10 | 10 | 10 | 10 | 10 | 10 | 10 | 10 |
| 24 | >100 | >100 | 10 | >100 | 10 | 50 | 50 | 10 | 50 |
| 25 | 100 | >100 | 10 | 100 | 10 | 50 | 10 | 10 | 50 |
| 3 | 10 | 10 | 10 | 10 | 10 | 10 | 10 | 10 | 10 |
| 37 | 10 | 10 | 10 | 10 | — | 10 | 10 | — | 10 |
| 27 | 10 | 10 | 10 | 10 | — | 10 | 10 | — | 10 |
| 45 | 10 | 10 | 10 | 10 | 10 | 10 | 10 | 10 | 10 |
| 1 | 10 | 10 | 10 | 10 | 10 | 10 | 10 | 10 | 10 |

From Table D, it can be seen that the compounds are also outstanding fungicides.

EXAMPLE 55

Determination of the action against algae (a) *Chlorella vulgaris*

A *Chlorella vulgaris* culture grown for 14 days in algae nutrient medium is diluted 1:200 in algae nutrient medium. Each of the compounds listed in Table E is then added such that a concentration of 3 mg/liter results. After incubation for 6 hours, 10 μl are in each case withdrawn and dripped onto algae agar in order to determine the destructive action. After incubation for 14 days with illumination (14 hours light/10 hours dark cycle), the growth in the algae medium (determination of the inhibition of growth) on the algae agar (determination of the algae-destruction action) is evaluated visually.

TABLE E

| | Action against *Chlorella vulgaris* | |
|---|---|---|
| | Growth | |
| No. | in the medium | on the agar |
| 5 | 1 | 2 |
| 20 | 1 | 2 |
| 21 | 1 | 2 |
| 22 | 1 | 2 |
| 23 | 1 | 2 |
| 24 | 1 | 2 |
| 25 | 1 | 2 |
| 8 | 1 | 2 |
| 3 | 1 | 2 |
| 37 | 1 | 2 |
| 27 | 1 | 2 |
| 45 | 1 | 2 |
| 1 | 1 | — |

1 = no growth in the medium, 3 ppm have a growth-inhibiting action
2 = no growth on the agar, 3 ppm have destroyed the algae within 6 hours.

(b) *Enteromorpha intestinalis*

The action against the green alga Enteromorpha most important in sea water fouling is investigated in sterile-filtered sea water containing Erd-Schreiber solution. The solution is composed of a nutrient extract, phosphate and nitrate. Incubation of the Enteromorpha intestinalis takes place in a light thermostat at 18° C. under a 14 hours light/10 hours dark cycle.

The algae grown in this manner are exposed for a short time (4 hours), in sea water, to the products to be investigated. The minimum killing concentration (MKC) is determined by removing the algae from the sea water containing a certain amount of algicide at the end of the period of action, washing them and investigating them for growth or destruction after renewed incubation in fresh sea water for 6 to 8 weeks.

The minimum killing concentration (MKC) is the amount of substance required to harm the alga within a certain period of time to the extent that it can no longer recover in fresh sea water and dies off.

To determine the inhibitory concentration (MIC), the alga is kept in sea water containing biocide throughout the entire duration of the experiment (concentration tested: 0.1 and 0.5 mg/liter).

TABLE F

| | Action against *Enteromorpha intestinalis* | |
|---|---|---|
| No. | Destruction 5 mg/liter | MIC (mg/liter) |
| 5 | yes | 0.5 |
| 20 | yes | >0.5 |

As can be seen from Tables E and F, the compounds have a marked algistatic and algicidal action against fresh water algae (for example treatment of cooling water) and sea water algae (for example growth protection for antifouling paints).

EXAMPLE 56

Determination of the action against *Artemia salina*

The commercially available eggs are caused to hatch under powerful aeration. The 2- to 3-day old nauplii are then exposed to various concentrations of the products (concentrations tested: 2.5; 1.5 and 2.25 mg/liter) in artificial sea water and are observed over a relatively long period of time.

TABLE G

| | Action against *Artemia salina* (about 30–50 *nauplii*) | | | | | | | | | | | |
|---|---|---|---|---|---|---|---|---|---|---|---|---|
| | 2.5 mg/liter | | | 1 mg/liter | | | 0.5 mg/liter | | | 0.25 mg/liter | | |
| No. | 6 hours | 24 hours | 48 hours | 6 hours | 24 hours | 48 hours | 6 hours | 24 hours | 48 hours | 6 hours | 24 hours | 48 hours |
| 2 | 3 | 3 | 3 | 2–3 | 3 | 3 | 2–3 | 3 | 3 | 2 | 3 | 3 |
| 5 | 2–3 | 3 | 3 | 2 | 3 | 3 | 1–2 | 2–3 | 3 | 1–2 | 3 | 3 |
| 20 | 1–2 | 3 | 3 | 2 | 2–3 | 3 | 1 | 2 | 3 | 0 | 1–2 | 2–3 |
| 21 | 1–2 | 3 | 3 | 1–2 | 3 | 3 | 1–2 | 2 | 3 | 1–2 | 3 | 3 |
| 22 | 1–2 | 3 | 3 | 1–2 | 3 | 3 | 1–2 | 3 | 3 | 0 | 1–2 | 2–3 |
| 23 | 1–2 | 3 | 3 | 1–2 | 3 | 3 | 1–2 | 2–3 | 3 | 0 | 1–2 | 2–3 |

0 = *nauplii* not affected
1 = slight change
1–2 = *nauplii* affected
2 = *nauplii* severely affected
2–3 = almost all *nauplii* dead
3 = all *nauplii* dead The outstanding action of the compounds against the salt-water crustacean can be seen from Table G. Artemia salina is related to the Balanidae, which cause the major problems of growth on ships.

Because of their activity against algae and against crustaceans, the compounds are suitable, inter alia, for finishing paint on ships.

Because of their broad action spectrum and their activity against bacteria, algae, fungi and crustaceans, these compounds are generally applicable for the preservation of materials, for example emulsion paints, antifouling paints, water treatment, wood preservation, boring and cutting oils, plastics, the paper industry and the like.

EXAMPLE 57.1

Action against Phytophtora infestans on Tomato plants (a) Residual curative action After being grown for 3 weeks, tomato plants were infected with a sporangia suspension of the fungus. After incubation for 22 hours in a humidity chamber at 90-100% relative atmospheric humidity and at 20° C., the infected plants were dried and were sprayed with a spray liquor (0.06% of active substance) prepared from a wettable powder of the active substance. After the spray coating had dried on, the treated plants were put back into the humidity chamber. The fungal attack was evaluated 5 days after the infection.

(b) Systemic action

After being grown for 3 weeks, tomato plants were watered with a spray liquor prepared from a wettable powder of the active substance (0.006% of active substance, based on the volume of soil). During watering, care was taken that the spray liquor did not come into contact with the above-ground parts of the plants. After 48 hours, the treated plants were infected with a sporangia suspension of the fungus. The fungal attack was evaluated after incubation of the infected plants at 90-100% relative atmospheric humidity and at 20° C. for 5 days.

EXAMPLE 57.2

Action against Cercospora arachidicola on ground nut plants (residual protection action)

Ground nut plants 10-15 cm high were sprayed with a spray liquor (0.02% of active substance) prepared from a wettable powder of the active substance, and 48 hours later were infected with a conidia suspension of the fungus. The infected plants were incubated at about 21° C. and at high atmospheric humidity for 72 hours and were then placed in a greenhouse until the typical leaf spots appeared. The fungicidal action was evaluated 12 days after the infection, and was based on the number and size of the spots which appeared.

EXAMPLE 57.3

Action against *Erysiphe graminis* on barley (residual protective action)

Barley plants about 8 cm high were sprayed with a spray liquor (0.02% of active substance) prepared from a wettable powder of the active substance. After 3-4 hours, the treated plants were dusted with conidia of the fungus. The infected barley plants were placed in a greenhouse at about 22° C. and the fungal attack was evaluated after 10 days.

In the preceding tests, compounds of the formula I showed a good fungicidal action. Thus, for example, with the compounds listed below, the attack was inhibited to less than 20%.
On *Phytophtora ifestans*: Nos. 5, 18 and 9.
On *Cercospora arachidicola*: Nos. 5, 7 and 9.
On *Erysiphe graminis*: No. 7.

EXAMPLE 58

Residual protective action against *Venturia inaequalis* on apple shoots

Apple cuttings with fresh shoots 10-20 cm long were sprayed with a spray liquor (0.02% of active substance) prepared from a wettable powder of the active substance. After 24 hours, the treated plants were infected with a conidia suspension of the fungus. The plants were then incubated at 90-100% relative atmospheric humidity for 5 days and were placed in a greenhouse at 20°-24° C. for 10 further days. The scab attack was evaluated 15 days after the infection. Compounds nos. 18, 5 and 9 and others inhibited the disease attack to less than 10%.

EXAMPLE 59

Action against moulds on moist maize

Dry maize grains (80 g portions) were thoroughly mixed with the test substance, in the form of an aqueous suspension, emulsion or solution, in plastic beakers which can be closed. Application of the substance was such that a concentration of 0.06% of active substance, based on the dry weight of maize, was achieved. A moistened flap of paper ensured a moisture-saturated atmosphere in the closed beakers.

Artificial infection was unnecessary. The extent of fungal development after 3 weeks was used to evaluate the activity of the test substance.

On treatment with compounds of the formula I, for example nos. 1 and 8, the attack was inhibited.

EXAMPLE 60

Growth on wood

Small wooden blocks of spruce, 7×10×10 mm in size, are dried under a vacuum for 30 minutes. The small blocks are then subjected to impregnation under a vacuum, by being left in 20 ml of distilled water and the biocide under vacuum for 30 minutes, and are then exposed to pressure treatment (2 atmospheres gauge by compressed air) in water for 18 hours. The pieces of wood thus treated are either immediately dried or first subjected to bleaching in running water and then dried.

The small dried pieces of wood are placed on potato glucose agar and the wood and surrounding agar are innoculated with 0.1 ml of a spore suspension of Aureobasidium pullans. After incubation at 28° C. for 4 weeks, the growth is evaluated according to the following plan.
2=Growth on the wood
3=No growth on the wood
4=No growth on the wood, inhibitory zone up to 2 mm
5=No growth on the wood, inhibitory zone greater than 2 mm

| Substance | Concentration not % in H₂O | not leached | leached for 5 days |
|---|---|---|---|
| 5 | 0.05 | 5 | 3-4 |
|   | 0.01 | 4 | 2 |
| 26 | 0.05 | 5 | 5 |
|   | 0.01 | 5 | 4 |
| 3 | 0.05 | 5 | 5 |
|   | 0.01 | 5 | 4 |

The outstanding action of the compounds in the preservation of wood, even after storage in water, can be seen from the Table.

What is claimed is:

1. A phosphonium stannate of the formula I

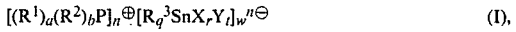

in which $R^1$ and $R^3$ are n-butyl, $R^2$ is $C_{12}$-$C_{16}$-alkyl, X and Y independently of one another are fluorine or chlorine, n is 1 or 2, q is 1, 2 or 3, a is 3 or 4, the value 4 only being permitted if X and/or Y are fluorine, b is 1 or 4, the value 4 only appearing if X and/or Y are fluorine, the sum (a+b) must always be 4, r and t are integers from 0 to 5, the sum (r+t) being 2 to 5 and the sum (q+r+t) corresponding to the value (n+4) and w is 1.

2. A compound according to claim 1, of the formula V $$[(C_4H_9)_3PR^2]^\oplus[(C_4H_9)_3SnCl_2]^\ominus \qquad (V),$$

in which the radical $R^2$ is $C_{12}$–$C_{14}$-alkyl.

3. A compound according to claim 1, of the formula VI $$[(C_4H_9)_3PR^2]^\oplus[(C_4H_9)_3SnF_2]^\ominus \qquad (VI),$$

in which $R^2$ is $C_{12}$–$C_{14}$-alkyl.

4. A compound of the formula VII $$[(C_6H_5)_3PR^2]^\oplus[(C_4H_9)_3SnCl_2]^\ominus \qquad (VII),$$

in which the radical $R^2$ is $C_{12}$–$C_{14}$-alkyl.

5. A compound of the formula VIII $$[(C_6H_5)_3PR^2]^\oplus[(C_4H_9)_3SnF_2]^\ominus \qquad (VIII),$$

in which the radical $R^2$ is $C_{12}$–$C_{14}$-alkyl.

* * * * *